United States Patent [19]

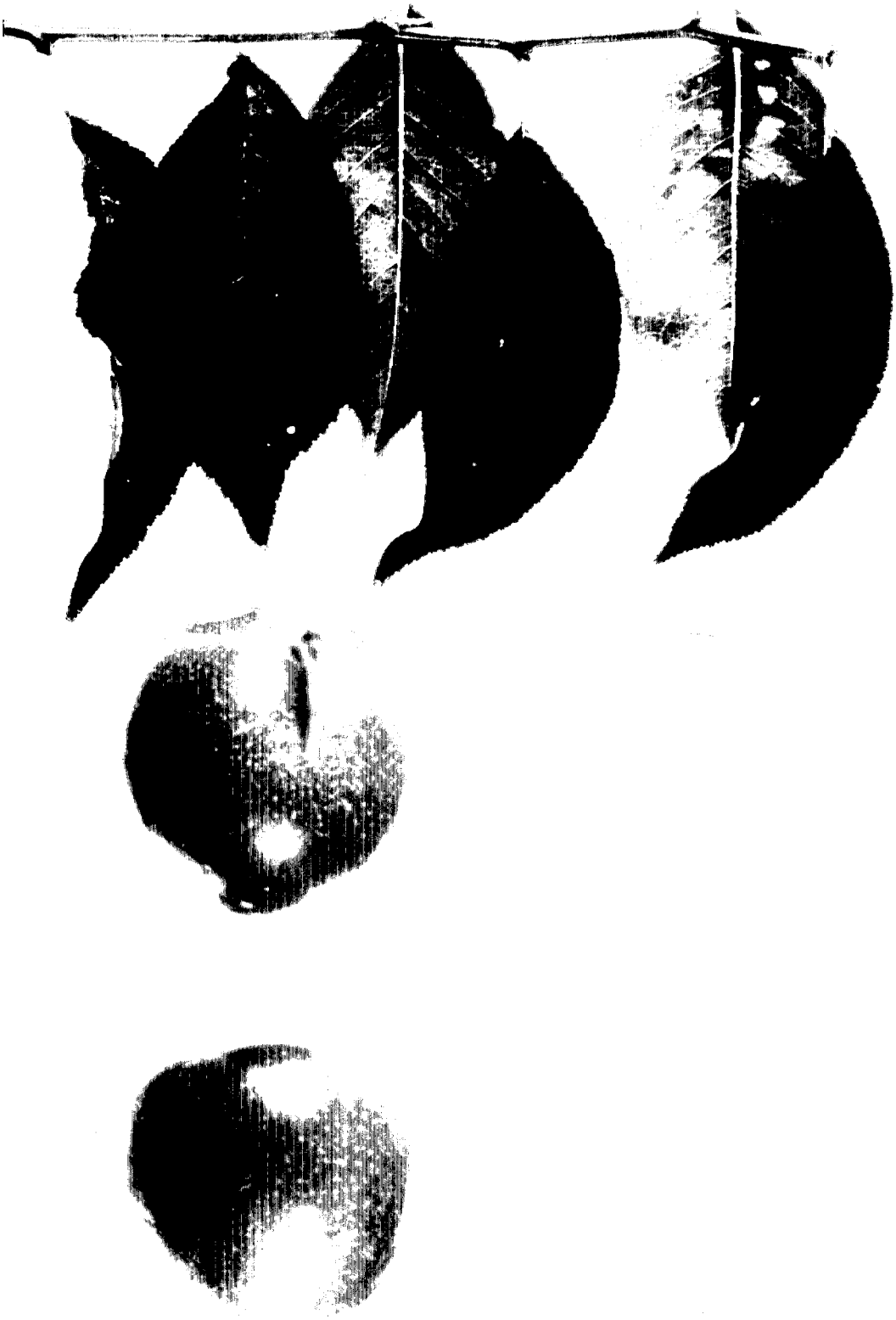

Zaiger et al.

[11] Patent Number: Plant 5,744

[45] Date of Patent: May 13, 1986

[54] PLUM TREE ("MID RED")

[76] Inventors: Chris F. Zaiger, 537 Rosemore Ave.; Leith M. Gardner, 1207 Grimes Ave.; Gary N. Zaiger, 1907 Elm Ave.; Grant G. Zaiger, 2121 Elm Ave., all of Modesto, Calif. 95351

[21] Appl. No.: 672,047

[22] Filed: Nov. 16, 1984

[51] Int. Cl.[4] ..... A01H 5/03

[52] U.S. Cl. ..... Plt./38

[58] Field of Search ..... Plt./38

*Primary Examiner*—Robert E. Bagwill

[57] ABSTRACT

A new and distinct variety of plum tree which is of medium to large size, vigorous, upright in growth, and a productive and regular bearer of large, firm, yellow flesh, clingstone fruit having a high degree of red skin color. The fruit is further characterized by relative uniform ripening throughout the tree, holding firm on the tree for 7–10 days after picking ripe, having good eating, shipping and storage quality.

1 Drawing Figure

ORIGIN OF THE VARIETY

The present variety of plum tree was originated by us in the experimental orchard located near Modesto, Calif. We selected it from a large number of seedlings which originated from a cross between a limb sport (which bore fruit with a higher degree of red skin color) of a Casselman Plum (Non-patented) and King David Plum (Non-patented). These seedlings which were planted and grown under careful observation by us, gave many and varying characteristics. One such seedling, which is the present variety, gave distinct and desirable characteristics and was selected for asexual reproduction and commercialization.

ASEXUAL REPRODUCTION OF THE VARIETY

The present variety of plum tree was asexually reproduced by budding in the experimental orchard located near Modesto, Calif. and shows that all characteristics come true to the original tree in all respects.

SUMMARY OF THE VARIETY

The new and distinct variety of plum tree which is medium to large, vigorous, upright in growth, and a regular and productive bearer of large, firm, yellow flesh, clingstone fruit ripening 7 to 10 days earlier than Casselman Plum (Non-patented); is further characterized in comparison by bearing fruit larger in size and with a higher degree of red skin color.

PHOTOGRAPHS OF THE VARIETY

The accompanying photographs show typical specimens of the foliage and fruit of my new plum variety, with the upper and lower surface of the leaves being illustrated and typical fruit specimens, an exterior and a sectional view being shown with a stone remaining in place. The illustrations were taken of the fruit shortly after being picked at maturity (firm ripe) and the colors are as nearly true as reasonably possible in a color representation of this type.

DESCRIPTION OF THE VARIETY

The following is a detailed description of the new variety of plum tree, its foliage and fruit based on observations of specimens grown at Modesto, Calif., with color terminology (except those in common color terms) in accordance with Reinhold Color Atlas by A. Kornerup and J. H. Wanscher.

Tree:
- *Size.*—Medium to large.
- *Vigor.*—Vigorous.
- *Form.*—Upright.
- *Density.*—Medium dense.
- *Production.*—Productive.
- *Bearing.*—Regular bearer.

Trunk:
- *Size.*—Stocky to medium.
- *Surface.*—Medium shaggy.
- *Color.*—Brownish gray.

Branches:
- *Size.*—Medium.
- *Texture.*—Rough.
- *Lenticels.*—Medium size. Medium number.
- *Color.*—Grayish brown to reddish brown.

Leaves:
- *Size.*—Average length — 4¼". Average width — 2".
- *Texture.*—Smooth. Medium length.
- *Petiole.*—Medium thickness.
- *Glands.*—Average number 2. Globose. Usually positioned on petiole, opposite, small.
- *Color.*—Upper surface — deep green (28-E-8) to (28-F-8). Lower surface — grayish green (29-E-5) to (29-E-7).
- *Form.*—Ovate — Acutely pointed.
- *Margin.*—Serrate.

Flower buds:
- *Size.*—Medium.
- *Length.*—Medium.

Flowers:
- *Blooming period.*—Date of first bloom: Mar. 6, 1983. Date of last bloom: Mar. 12, 1983. Late as compared to other varieties.
- *Color.*—White.
- *Size.*—Medium, non-showy.

Fruit:
- *Maturity when described.*—Firm ripe.
- *Date of first picking.*—Aug. 9, 1983.
- *Date of last picking.*—Aug. 11, 1983.
- *Size.*—Large. Average diameter axially — 2½". Average transversely in suture plane — 2 5/16".
- *Form.*—Slightly elongated. Uniform.

*Suture.* —Shallow extends from base to apex.
*Ventral surface.*—Rounded — Vary slightly lipped.
*Cavity.*—Rounded. Average depth — $\frac{5}{8}$" Average breadth — $\frac{5}{8}$".
Base.—Retuse.
*Apex.*—Rounded to slight depression.

Skin:
*Thickness.*—Medium.
*Tenacity.*—Tenacious to flesh.
*Texture.*—Smooth.
*Tendency to crack.*—Very slight.
*Down.*—Wanting.
*Color.*—Yellow ground color (4-A-8) to (4-B-8). Overspread with red (10-B-8) to (10-C-8). Numerous small dots of yellow ground color.

Flesh:
*Juice.*—Moderate.
*Texture.*—Firm and meaty.
*Ripens.*—Evenly.
*Flavor.*—Sub-acid to mild.
*Eating quality.*—Good.
*Color.*—Mellow yellow (5-A-6) to golden yellow (5-B-7).

Stone:
*Type.*—Clingstone.
*Size.*—Average length — 1". Average width — 9/16". Average thickness — $\frac{1}{2}$".
*Form.*—Usually ovid — Width at base varies slightly.

*Base.*—Straight to slightly oblique.
*Apex.*—Acute.
*Sides.*—Nearly equal.
*Surface.*—Irregularly furrowed.
*Ventral edge.*—Thin.
*Dorsal edge.*—Broad grooved wing usually near base.
*Tendency to split.*—None.

Use: Dessert.
*Market.*—Local and long distance shipping.
Keeping quality: Good.
Shipping quality: Good.

The plum tree and its fruit herein described may vary in slight detail due to the climatic and soil conditions in which the variety may be grown; the present description being that of the new variety grown under the ecological conditions prevailing at Modesto, Calif.

The following is claimed:

1. A new and distinct variety of plum tree, substantially as illustrated and described, which is a productive and regular bearer of large, yellow flesh, clingstone fruit with good eating, shipping and storage quality; the fruit is further characterized, in comparison to Casselman Plum (Non-patented) by ripening 7 to 10 days earlier, being larger in size and having a higher degree of red skin color.

* * * * *